US00PP14515P29

(12) United States Plant Patent
Zaiger et al.

(10) Patent No.: US PP14,515 P2
(45) Date of Patent: Feb. 3, 2004

(54) PEACH TREE NAMED 'SWEET SHASTA'

(50) Latin Name: *Prunus persica*
Varietal Denomination: Sweet Shasta

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/313,578

(22) Filed: Dec. 9, 2002

(51) Int. Cl.[7] ..... A01H 5/00
(52) U.S. Cl. ..... Plt./198
(58) Field of Search ..... Plt./198

*Primary Examiner*—Bruce R. Campell
*Assistant Examiner*—Anne Marie Grunberg

(57) ABSTRACT

A new and distinct variety of peach tree (*Prunus persica*), which has the following unique combination of features that are desirable in a new variety.

1. Fruit with a mild, sub-acid, sweet flavor.
2. Fruit with firm, yellow flesh, good handling and shipping quality.
3. Fruit that will stay firm on the tree 6 to 8 days after maturity.
4. Fruit with an attractive red skin color.
5. Vigorous, upright growth of tree.
6. Having a low winter chilling requirement of approximately 350 hours.
7. Heavy and regular production of fruit.

1 Drawing Sheet

BACKGROUND OF THE VARIETY

In the field of plant genetics, we conduct an extensive and continuing plant-breeding program including the organization and asexual reproduction of orchard trees, of which plums, peaches, nectarines, apricots, cherries and interspecifics are exemplary. It is against this background of our activities that the present variety of peach tree was originated and asexually reproduced by us in our experimental orchard located near Modesto, Stanislaus County, Calif.

PRIOR VARIETIES

Among the existing peaches and nectarines known to us, and mentioned herein; 'Early Sun Grand' Nectarine (U.S. Plant Pat. No. 1,420), 'Sun Red' Nectarine (non-patented), 'O'Henry' Peach (U.S. Plant Pat. No. 2,964), 'Sweet Gem' Peach (U.S. Plant Pat. No. 7,952), 'Spring Crest' Peach (non-patented) and 'Desert Gold' Peach (non-patented).

STATEMENT REGARDING FEDERALLY SPONSORED RESEARCH OR DEVELOPMENT

Not applicable.

ORIGIN OF THE VARIETY

The new variety of peach tree (*Prunus persica*) was originated by us in our experimental orchard located near Modesto, Calif. from a first generation cross between two proprietary seedlings with field identification numbers (88ED70) and (7LA283). The maternal parent (88ED70) was originated by us from crosses between the following varieties; 'Early Sun Grand' Nectarine (U.S. Plant Pat. No. 1,420). 'Desert Gold' Peach (non-patented), 'O'Henry' Peach (U.S. Plant Pat. No. 2,964) and 'Sweet Gem' Peach (U.S. Plant Pat. No. 7,952). The pollen parent (7LA283) originated from a cross between 'Sun Red' Nectarine (non-patented) and 'Spring Crest' Peach (non-patented). A large group of these first generation seedlings were planted and grown on their own root system under careful and close observation. One such seedling, which is the present variety, exhibited desirable tree growth and fruit characteristics and was selected in 1992 for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us, in our experimental orchard located near Modesto, Calif., and shows that all characteristics of the tree and its fruit run true to the original tree and are established and transmitted through succeeding asexual propagations.

SUMMARY OF THE VARIETY

The new variety of peach tree is of large size, vigorous, upright growth and a productive and regular bearer of large, firm, yellow flesh, freestone fruit, having a mild, sub-acid, sweet flavor with very good eating quality. The fruit is further characterized by having an attractive red skin color, being relatively uniform in size throughout the tree and holding firm on the tree 6 to 8 days after maturity (shipping ripe). The tree having a low winter chilling requirement of approximately 350 hours and, in comparison to the low chilling variety parent 'Desert Gold' Peach (non-patented), the fruit of the new variety is larger in size, has firmer flesh with greater storage and shipping quality, has a more attractive red skin color and is approximately 18 days later in maturity.

PHOTOGRAPH OF THE VARIETY

The accompanying color photographic illustration shows typical specimens of the fruit and foliage of the new peach variety. The illustration shows the upper and lower surface of the leaves, an exterior and sectional view of a fruit divided in its suture plane to show flesh color, pit cavity and a stone remaining in place. The photographic illustration was taken shortly after being picked (shipping ripe) and the colors are as true as is reasonably possible in a color representation of this type.

DESCRIPTION OF THE VARIETY

The following is a detailed botanical description of the new variety of peach tree, its flowers, foliage and fruit, as based on observations of 8 year old specimens budded to 'Nemaguard' Rootstock (non-patented) and grown near Modesto, Calif., with color in accordance with Munsell Book of Color.

Tree:

*Size.*—Large, normal for peach trees. Pruned to 3 to 3.5 meters in height at maturity.

*Vigor.*—Vigorous. Tree growth of 1.5 to 2 meters in height the first growing season. Varies with fertility, type of soil and cultural practices.

*Form.*—Upright, usually pruned to vase shape.

*Productivity.*—Productive. Normal fruit thinning and spacing necessary. Number of fruit set per tree varies with climatic conditions during blooming period.

*Bearer.*—Regular. Adequate fruit set for 5 consecutive years. No alternate bearing observed.

*Fertility.*—Self-fertile.

*Density.*—Medium dense. Pruning to open center of tree (vase shape) is desirable to enhance fruit color and keep fruit wood healthy.

*Hardiness.*—Tree grown in USDA Hardiness Zone 9. Winter chilling requirement approximately 350 hours at or below 45° F.

Trunk:

*Size.*—Large, stocky. Measured 50.8 cm in circumference at 30.5 cm above the ground on an 8 year old tree.

*Texture.*—Medium shaggy, becomes rougher with age of tree.

*Color.*—Varies from l0YR 3/2 to 10YR 5/2.

Branches:

*Size.*—Medium. Average 19.7 cm at 1 meter above the ground.

*Surface texture.*—New growth smooth, varies to medium rough with age of growth.

*Lenticels.*—Average number 51 in a 25.8 square cm area. Average length 4.2 mm. Average width 1.5 mm. Color 7.5YR 6/10.

*Color.*—New growth 2.5GY 6/6 to 2.5GY 5/6. Old growth 2.5Y 4/4 to 2.5Y 5/4, becoming darker with age.

Leaves:

*Size.*—Medium to large. Average length 134.7 mm. Average width 37.8 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Average length 11.6 mm. Average width 1.9 mm. Color varies from 2.5GY 6/8 to 2.5GY 5/6. Grooved longitudinally. Glabrous.

*Glands.*—Reniform. Size varies from small to medium. Average length 0.8 mm. Average diameter 0.5 mm. Number varies from 3 to 4. Located on base of leaf blade and upper portion of petiole. Color varies from 5R 3/6 to 5R 4/8.

*Color.*—Upper surface 5GY 3/4 to 5GY 3/6. Lower surface 5GY 5/4 to 5GY 4/6.

Flower buds:

*Size.*—Large. Average length 20.1 mm. Average width 10.2 mm.

*Hardiness.*—Hardy in all stone fruit growing areas of California.

*Pedicel.*—Average length 4.1 mm. Average width 1.3 mm. Color varies from 2.5GY 6/6 to 2.5GY 6/8.

*Form.*—Plump, conical, becomes elongated before opening.

*Color.*—Varies from 2.5RP 8/6 to 5RP 6/8.

Flowers:

*Size.*—Large, showy. Average height 19.5 mm. Average diameter 33.7 mm.

*Blooming period.*—Date of First Bloom Feb. 18, 2002. Date of Petal Fall Feb. 28, 2002. Varies slightly with climatic conditions.

*Petals.*—Number 5, alternately arranged to sepals. Large size. Average length 21.2 mm. Average width 21.3 mm. Orbicular, apex rounded. Margin — sinuate, slightly cupped. Both upper and lower surfaces glabrous. Color varies from 5RP 9/2 to 5RP 8/6.

*Sepals.*—Number 5, alternately arranged to petals. Ovate, apex rounded. Upper surface glabrous, lower surface pubescent. Color — upper surface varies from 2.5GY 6/8 to 5RP 5/6. Lower surface varies from 7.5RP 3/4 to 7.5RP 3/6.

*Stamens.*—Average number per flower 44. Average filament length 16.4 mm. Filament color varies from 10RP 9/2 to 5RP 7/8. Anther color varies from 2.5R 3/10 to 5R 3/10.

*Pollen.*—Self fertile. Color 5Y 8/10.

*Pistil.*—Number — normally one. Surface — pubescent. Average length 18.6 mm. Position of stigma — average of 1.9 mm above anthers. Color varies from 10Y 8/6 to 10Y 8.5/6.

*Fragrance.*—Slight.

*Pedicel.*—Average length 4.1 mm. Average width 1.3 mm. Color varies from 10Y 7/8 to 10Y 6/8.

*Number of flowers per bud.*—One.

*Color.*—Varies from 5RP 8/6 to 5RP 7/6.

Fruit:

*Maturity when described.*—Firm ripe.

*Date of first picking.*—Jul. 5, 2002.

*Date of last picking.*—Jul. 13, 2002. Varies slightly with climatic conditions.

*Size.*—Large. Average diameter axially 74.4 mm. Average transversely in suture plane 83.6 mm. Average weight 269.8 grams, weight varies slightly with number of fruit per tree, fertility of soil and climatic conditions.

*Form.*—Globose.

*Suture.*—Shallow, extends from base to apex.

*Ventral surface.*—Nearly rounded, surface slightly enlarged.

*Apex.*—Flattened to slightly retuse.

*Base*.—Retuse.
*Cavity*.—Rounded to slightly elongated in suture plane. Average depth 10.4 mm. Average breadth 19.3 mm.

Stem:
*Size*.—Medium. Average length 11.5 mm. Average width 3.4 mm.
*Color*.—Varies from 5GY 6/6 to 5GY 6/8.

Flesh:
*Ripens*.—Evenly.
*Texture*.—Firm, meaty.
*Fibers*.—Few, small and tender.
*Aroma*.—Slight.
*Flavor*.—Very good.
*Color*.—Yellow, varies from 5Y 8.5/8 to 5Y 8.5/12. Pit cavity varies from 7.5R 4/10 to 7.5R 4/12. Slight bleeding from pit cavity into flesh.
*Amydgalin*.—Undetected.
*Eating quality*.—Very good.
*Juice*.—Moderate, enhances flavor.
*Brix*.—Average 12.3°.

Skin:
*Thickness*.—Medium.
*Surface*.—Smooth.
*Down*.—Moderate amount, short in length.
*Tendency to crack*.—None.
*Color*.—Ground color varies from 5Y 8.5/8 to 5Y 8.5/10. Nearly overspread with 7.5R 5/10 to 7.5R 4/10.
*Tenacity*.—Tenacious to flesh.
*Astringency*.—None.

Stone:
*Type*.—Freestone.
*Size*.—Large. Average length 32.5 mm. Average width 27.0 mm. Average depth 21.9 mm.
*Form*.—Ovoid.
*Base*.—Flat to slightly rounded.
*Apex*.—Pointed, average length 1.9 mm.
*Surface*.—Irregularly furrowed toward apex, pitted toward base. Pit cavities vary from round to elongated. Ridges slightly narrow with rough surface.
*Sides*.—Unequal, with one side slightly larger, extending further from suture plane.
*Tendency to split*.—Very slight.
*Color*.—Varies from 10R 4/8 to 2.5YR 5/8 when dry.

Kernal:
*Size*.—Medium. Average length 16.5 mm. Average width 10.2 mm. Average depth 7.0 mm.
*Color*.—Varies from 2.5Y 8.5/4 to 5Y 9/6 when dry.
*Viability*.—Viable, embryo nearly developed.
*Taste*.—Bitter.
*Form*.—Ovate.

Use: Dessert. Market — local and long distance.

Keeping quality: Good, held firm in cold storage at 38° to 42° F. for 21 days without internal flesh breakdown or appreciable loss of flavor.

Shipping quality: Minimal skin scarring or bruising of flesh during picking and packing trials.

Plant disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth and being a productive and regular bearer of large, yellow flesh, freestone fruit with a mild, sweet, sub-acid flavor with very good eating quality; the fruit is further characterized by having firm flesh with good storage and shipping quality, having an attractive red skin color and, in comparison to 'Desert Gold' Peach (non-patented), the fruit has firmer flesh, a more attractive red skin color and is approximately 18 days later in maturity.

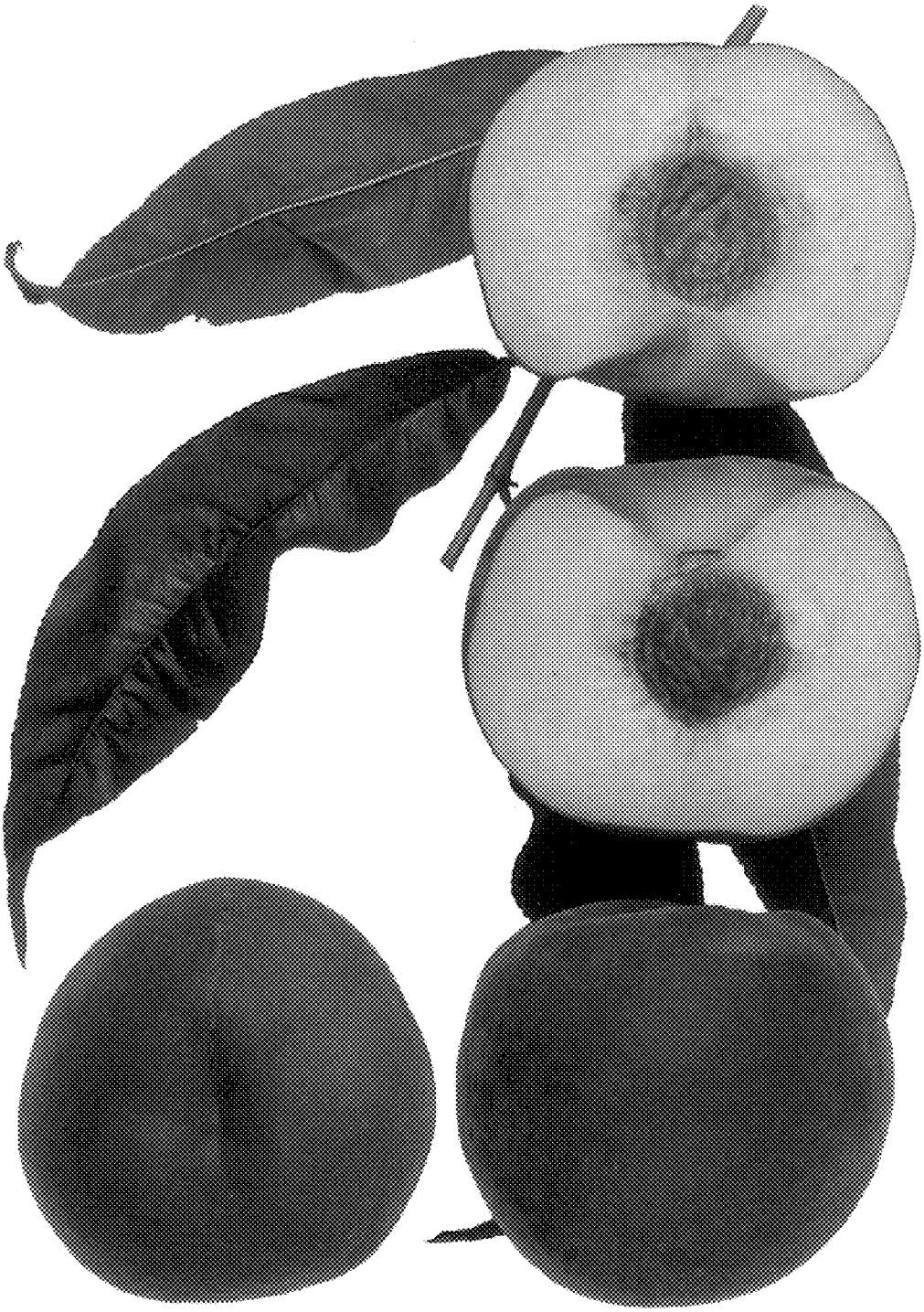

* * * * *